US00PP16047P2

(12) United States Plant Patent
Vijverberg

(10) Patent No.: US PP16,047 P2
(45) Date of Patent: Oct. 18, 2005

(54) ***CHRYSANTHEMUM* PLANT NAMED 'CEVYKING DARK'**

(50) Latin Name: *Chrysanthemum morifolium*
Varietal Denomination: Cevyking Dark

(75) Inventor: Arnold G. P. Vijverberg, 's-Gravenzande (NL)

(73) Assignee: Chrysanthemum Breeders Assoc. NV (NL)

( * ) Notice: Subject to any disclaimer, the term of this patent is extended or adjusted under 35 U.S.C. 154(b) by 86 days.

(21) Appl. No.: 10/872,435

(22) Filed: Jun. 22, 2004

(51) Int. Cl.[7] ..... A01H 5/00
(52) U.S. Cl. ..... Plt./295
(58) Field of Search ..... Plt./295

*Primary Examiner*—Anne Marie Grunberg
(74) *Attorney, Agent, or Firm*—Parkhurst & Wendel, L.L.P.

(57) ABSTRACT

A *Chrysanthemum* plant named 'Cevyking Dark' characterized by its small sized single-type blooms with yellow ray-florets and dark brown center, with a response time of 56 days.

3 Drawing Sheets

RELATED CULTIVARS

'Cevyking Dark' is a sport of the variety 'Cevyking' (U.S. Plant patent application Ser. No. 09/708,588), which is also the parent of the variety 'Vyking Orange Dark' (U.S. Plant Pat. No. 14,055).

BACKGROUND OF THE INVENTION

'Ceyking Dark' is a product of a breeding and selection program which had the objective of finding color mutants of 'Cevyking' with a dark center of the blooms. The new plant of the present invention comprises a new and distinct cultivar of *Chrysanthemum* plant that is a natural occurring sport of a parent *Chrysanthemum* named 'Cevyking'. A comparison with parent *Chrysanthemum* 'Cevyking' is also made in this application. The new cultivar was discovered as a whole plant mutation in 2001 by Arnold G. P. Vijverberg in a controlled environment (greenhouse) in 's-Gravenzande, Holland. The first act of asexual reproduction of 'Cevyking Dark' was accomplished when vegetative cuttings were taken and propagated from the initial selection in 2001 in 's-Gravenzande Holland.

SUMMARY OF THE INVENTION

The present invention is a new and distinct variety of *Chrysanthemum* bearing small sized blooms with yellow ray-florets and a dark brown center.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
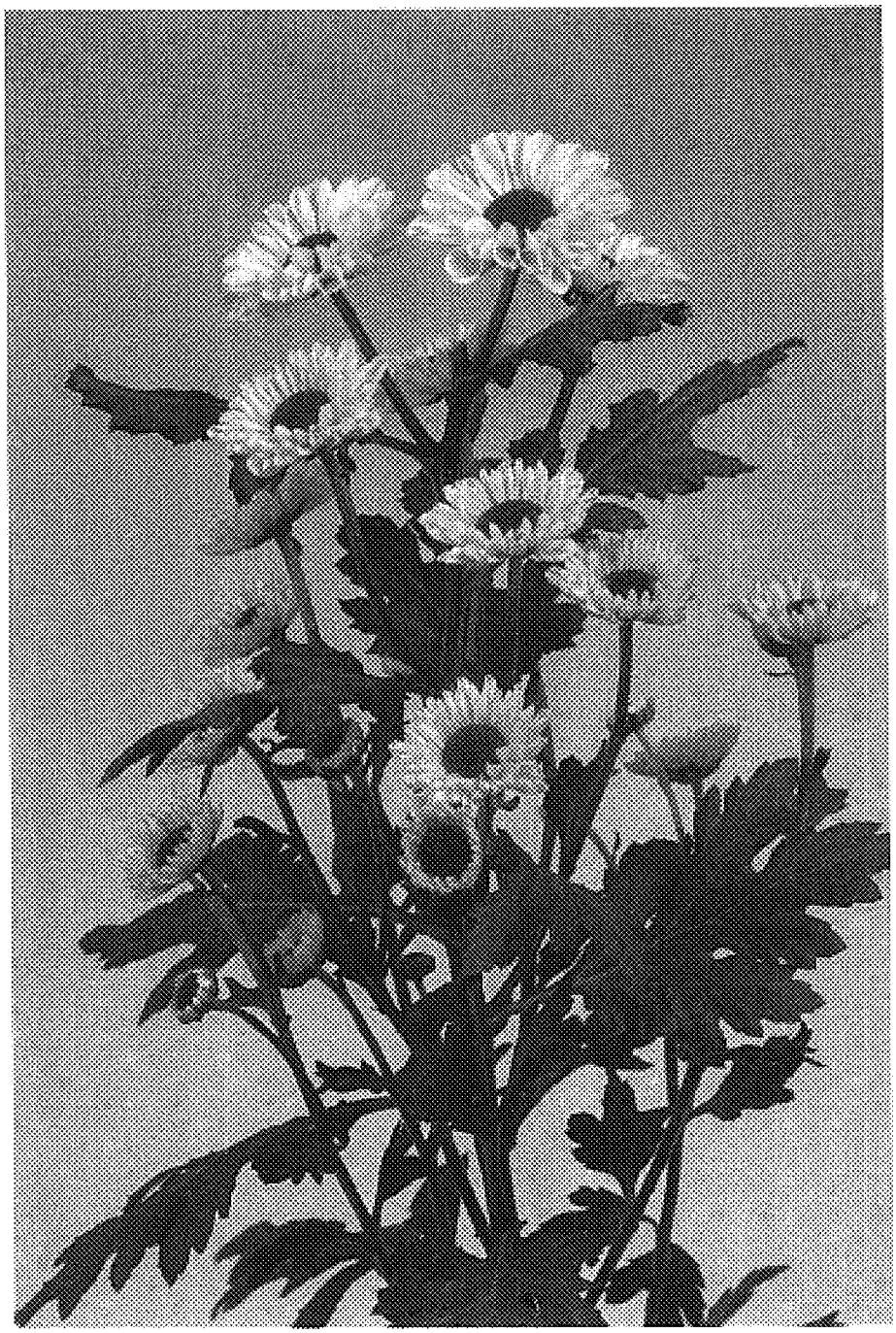
FIG. 1 shows a plant of the cultivar in full bloom.
Figure 2:
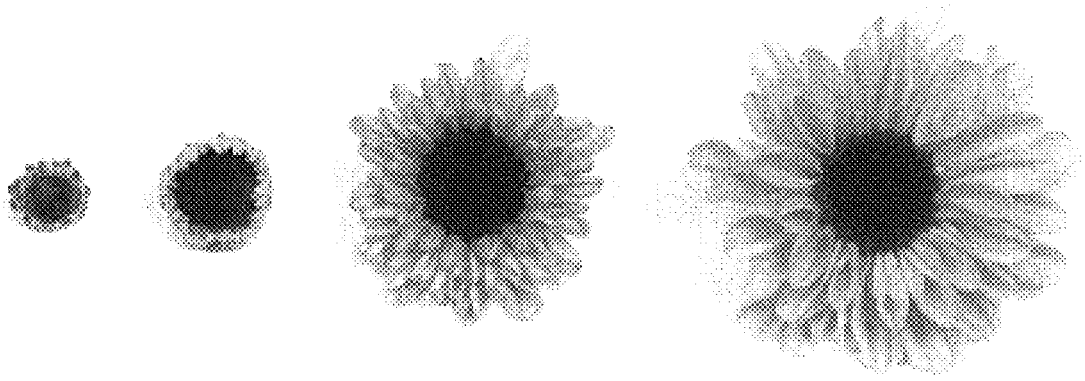
FIG. 2 shows the various stages of bloom of the new cultivar.
Figure 3:
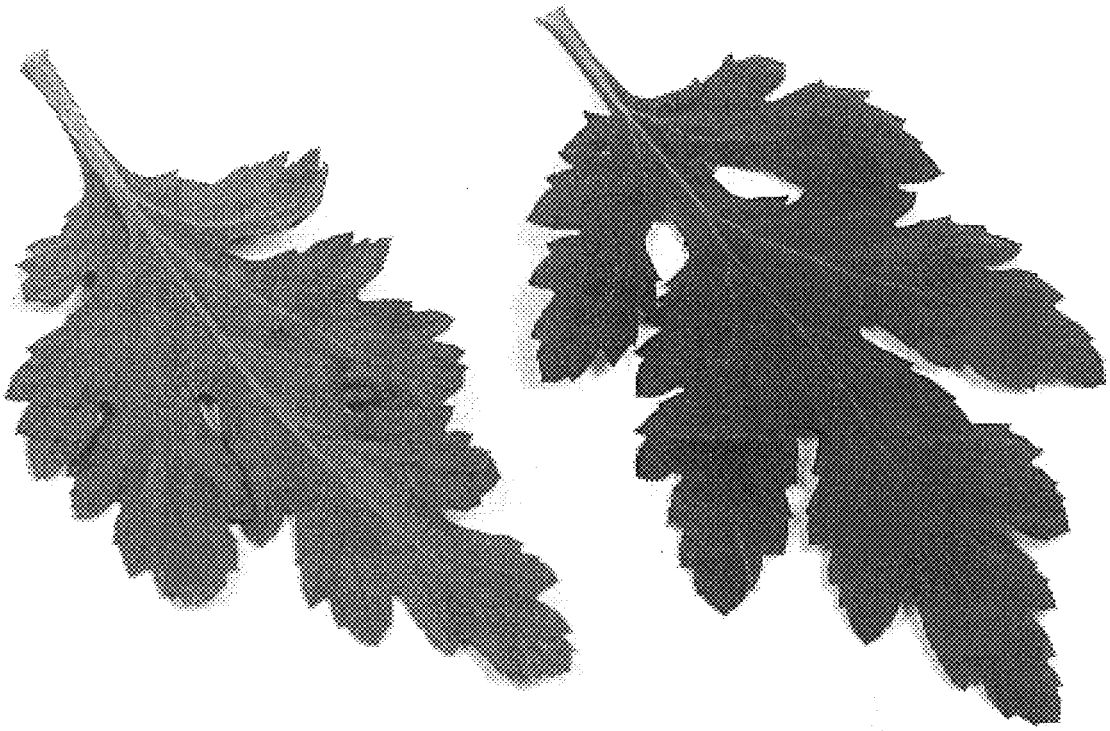
FIG. 3 shows the foliage of the new cultivar.

This new variety of *Chrysanthemum* is of the botanical classification *Chrysanthemum morifolium* L. The observations and measurements were gathered from plants grown in April/May in a greenhouse in Rijsenhout, Holland in a photo-periodic controlled crop under conditions generally used in commercial practice. The greenhouse temperatures during this crop were at day-time between 18° C. and 25° C. and at night 20° C. After a long day period of 14 days, the photo-periodic response time in this crop was 56 days. After the long day period to flowering, growth retardants were applied 2 to 3 times in an average dose of 2.5 gram/liter water. Plants of the new variety are sensitive to infestation by insects like thrips. No tests were done on cold or drought resistance. This new variety produces small sized blooms with yellow ray-florets and dark brown disc-florets blooming on the plant for 3 weeks. This new variety of *Chrysanthemum* has been found to retain its distinctive characteristics throughout successive propagations however the phenotype may vary significantly with variations in environment such as light intensity and temperature. To show the phenotype as described 'Cevyking Dark' can be planted without assimilation lightning (high pressure sodium lamps) between week 1 and week 36. under greenhouse conditions in Holland. With assimilation light (minimum level 2500 lux) it can be planted year round under greenhouse conditions in Holland.

From the cultivars known to inventor the most similar existing cultivar in comparison to 'Cevyking Dark' is the parent 'Cevyking', and 'Vyking Orange Dark' which is also a sport of 'Cevyking'. When 'Cevyking', 'Cevyking Dark' and 'Vyking Orange Dark' are being compared the following differences and similarities are noticed: The differences of 'Cevyking', 'Cevyking Dark' and 'Vyking Orange Dark' are (1) Color tip of disc-florets. The tip of the disc-florets of the parent variety 'Cevyking' is brown and fading to green-brown in summer, while the tips of 'Cevyking Dark' are dark brown all year round. The tip of the disc-florets of 'Vyking Orange Dark' is light brown. (2) Color ray-florets. The color of the ray-florets of both 'Cevyking' and of 'Cevyking Dark' are yellow, while it is orange in 'Vyking Orange Dark'. (3) Number of blooms per stem. The parent plant 'Cevyking' and 'Vyking Orange Dark' has on average a smaller number of blooms than 'Cevyking Dark'. For which characteristics 'Cevyking Dark' has been selected out of 'Cevyking'. All other characteristics of 'Cevyking' and 'Cevyking Dark' are similar.

The following is a description of the plant and characteristics that distinguish 'Cevyking Dark' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of cultivar 'Cevyking Dark' | |
|---|---|
| Bud | |
| Size | Medium, cross-section 1.5 cm height 1.2 cm |
| Outside color | Yellow-orange 15B |
| Involucral bracts | 2 rows, length 7 mm, width 3 mm |
| Involucral bracts among disc-florets | Not present |
| Involucral bracts color | Yellow-green 146A |
| Inflorescence | |
| Type | Single |
| Height | 1.3–1.7 cm |
| Size | Small |
| Fully Expanded | 4–4.5 cm |
| Peduncle length | Near the top 6 cm, near the middle 12 cm, near the bottom 16 cm |
| Peduncle color | Yellow-green 146A |
| Number of blooms per stem | Average of 12 |
| Performance on the plant | 21 days |
| Seeds (if crossed) | Produced in small quantities, oval shaped, grey-brown 199A, 2 mm in length. |
| Fragrance | Typical *chrysanthemum* |
| Color | |
| Center of the flower (disc-florets) | Immature Brown 200A<br>Mature Brown 200A |
| Color of upper surface of the ray-florets | Upper surface Yellow 12A<br>Lower surface Yeltow 7A |
| Tonality from Distance | A spray mum with yellow flowers and a dark brown disc |
| Color of the upper surface of the ray florets after aging of the plant | Yellow 12A |
| Ray florets | |
| Texture | Upper and under side smooth |
| Number | 55–65, three rows |
| Cross-section | Concave, one keel |
| Longitudinal axis of majority | Straight |
| Length of corolla tube | Short, 0.4–0.6 cm |
| Ray-floret margin | Entire |
| Ray-floret length | 1.5–2.0 cm |
| Ray-floret width | 0.5–0.7 cm |
| Ratio length/width | Medium |
| Shape of tip | Rounded, sometimes dentate |
| Disc florets | |
| Disc diameter | 1.5 cm |
| Distribution of disc florets | Numerous clearly visible at all stages of flowering. |
| Shape | Tubular |
| Color | Yellow-green 145C at base, Yellow 13B in middle part and Brown 200A at tip |
| Receptacle shape | Conical raised |
| Reproductive Organs | |
| Stamen (present in disc florets only) | Thick, 4 mm in length |
| Number of stamen | 4 |

TABLE 1-continued

| Botanical Description of cultivar 'Cevyking Dark' | |
|---|---|
| Stamen color | Yellow-green 144A |
| Pollen | Not present |
| Styles (present in both ray and disc florets) | Thick |
| Style color | Yellow-green 145D |
| Style Length | 5 mm |
| Stigma color | Yellow-green 145D |
| Stigma Width | 1 mm |
| Ovaries | Enclosed in perianth |
| Plant | |
| Form | A spray mum meant for erect culture |
| Growth habit | Upright |
| Growth rate | Slow |
| Height | 100 cm |
| Width | 18–20 cm |
| Internode length | 2.5–3 cm |
| Spray formation | Corymbiform |
| Stem Color | Yellow-green 146A |
| Stem Strength | Strong |
| Stem Brittleness | Present |
| Stem Anthocyanin Coloration | Present, a thin layer of Greyed-red 181A |
| Flowering Response(photo-periodic controlled crop, not natural season) | 56 Days |
| Foliage | |
| Color immature stage | Upper side Yellow-green 146A<br>Under side Yellow-green 146B |
| Color mature stage | Upper side Yellow-green 147A<br>Under side Yellow-green 147B |
| Color midvein | Upper side Yellow-green 146B<br>Under side Yellow-green 146C |
| Size | Large; length 12 cm, width 7 cm |
| Quantity (number per single stem) | 30–32 |
| Shape | Ovate |
| Texture upper side | Fleshy and glabrous |
| Texture under side | Pubescent |
| Venation arrangement | Palmate |
| Shape of the margin | Crenated |
| Shape of Base of Sinus Between Lateral Lobes | Round |
| Margin of Sinus Between Lateral Lobes | Converging |
| Shape of Base | Truncate |
| Apex | Mucronate |
| Petiole length | 2.0 cm |
| Petiole color | Yellow-green 146B |

TABLE 2

| Differences with the comparison Variety | | | |
|---|---|---|---|
| | 'Cevyking Dark' | 'Cevyking' | 'Vyking Orange Dark' |
| Color tip disc-florets | Brown 200A | Greyed Orange 166A | Greyed Orange 166A |
| Color ray-florets | Yellow 12A | Yellow 12A | Greyed Orange 169C |
| Number of blooms per stem | 12 | 8 | 8 |

I claim:

1. A new and distinct variety of *Chrysanthemum* plant as described and illustrated.

* * * * *